United States Patent [19]

Best

[11] Patent Number: 4,770,052

[45] Date of Patent: Sep. 13, 1988

[54] CALCULATING AEROSOL DROPLET DIMENSIONS

[76] Inventor: Mark P. Best, 146 Caversham Valley Road, Dunedin, New Zealand

[21] Appl. No.: 737,414

[22] Filed: May 25, 1985

[30] Foreign Application Priority Data

May 24, 1984 [NZ] New Zealand ................... 208274

[51] Int. Cl.$^4$ .............................................. G01N 15/02
[52] U.S. Cl. .................................................. 73/865.5
[58] Field of Search ....................................... 73/865.5

[56] References Cited

U.S. PATENT DOCUMENTS

| | | | |
|---|---|---|---|
| 3,693,457 | 9/1972 | Pilat ..................................... | 73/865.5 |
| 3,854,321 | 12/1974 | Dahneke ............................. | 73/865.5 |
| 3,877,311 | 4/1975 | Sugawara et al. .................. | 73/865.5 |
| 4,265,107 | 5/1981 | Cheng et al. ........................ | 73/865.5 |

OTHER PUBLICATIONS

Mark P. Best, "Electron Microscopic Measurement of Droplet Size Parameters . . .," *Australia and New Zealand J. of Med.*, vol. 15(4), p. 568, 1985.
Seager et al, "Structure of Products Prepared by Freeze-Drying Solutions Containing Organic Solvents", *J. of Parenteral Sci. and Technology*, vol. 39, No. 4, pp. 161–179, 1985.
Best et al, "Demonstration of Mucociliary Clearance in Ventilation Scintigraphy Using an Airjet Nebulizer," *Clinical Nuclear Medicine*, vol. 10, No. 4, Abstract, Apr. 1985.

*Primary Examiner*—Stewart J. Levy
*Assistant Examiner*—Robert R. Raevis
*Attorney, Agent, or Firm*—Birch, Stewart, Kolasch & Birch

[57] ABSTRACT

Aerosol droplet dimensions are important when aerosols are used as delivery means for such as labelled antibodies. Droplets from an aerosol containing solvent and solute are deposited onto a surface, which surface permits the droplet to maintain its surface tension, and subjected to rapid freeze drying. The solvent is vaporized while the solute forms a crystal lattice, which is treated and subjected to analysis which permits an estimate of the original droplet dimensions.

14 Claims, 7 Drawing Sheets

AEROSOL DROPLET SIZE DISTRIBUTION NEBULISER

DROPLET DIAMETER/MICRONS

AEROSOL DROPLET SIZE DISTRIBUTION NEBULISER

DROPLET DIAMETER/MICRONS

FIG. 1

AEROSOL DROPLET SIZE DISTRIBUTION
SCINTIGRAPHIC NEBULISER

DROPLET DIAMETER / MICRONS

FIG. 2

DIAGRAMMATIC REPRESENTATION OF A FREEZE DRIER
MACROSCOPIC DROPLET SOLUTE CRYSTAL RESIDUES
DEMONSTRATING FLUIDIC EUTECTIC NATURE
OPTICAL PHOTOGRAPH--MAGNIFICATION 5X. ALSO
UTILIZED IN SPREAD FACTOR

AEROSOL SAMPLE GOLD COATING DEPOSITER FOR SEM
eg. Diode Sputtering

FIG. 6

BLOCK DIAGRAM OF SCANNING
ELECTRON MICROSCOPE

CALCULATING AEROSOL DROPLET DIMENSIONS

BACKGROUND OF THE INVENTION

This invention relates to a method of calculating aerosol droplet size, and more particularly to a method of analyzing aerosol sprays having a selected droplet size.

The use of aerosols for diagnostic and thereapeutic uses is known. Yeates D B, et al, (Journal of Applied Physiology Vol 39 No. 3 September 1975) teach the use of radio labelled aerosols for measuring mucociliary tracheal transport. The use of aerosols as a drug-delivery system in bronchial complaints is also well known.

It is well known that aerosol droplet size is important in these uses for aerosols. It is also known that large droplets tend to impact in the upper airways and throats of subjects. Small droplets tend to deposit on the alveolar surfaces. Various of the said uses for aerosols require aerosols with particular droplet dimensional characteristics for optimum efficiency, which, if achieved, reduce subject discomfort, the amount of equipment and materials used, running costs, and time expended.

Previous methods of measuring aerosol droplet dimensions have included light photometry. However, the accuracy of such methods has not always been as good as is desired.

Accordingly, it is an object of this invention to provide a method of accurately calculating and analyzing the droplet dimensions of an aerosol sample.

SUMMARY OF THE INVENTION

According to the invention there is provided a method for calculating droplet dimensions of an aerosol containing inter alia a solution including:

removing solvent from droplets of an aerosol sample whilst retaining substantially all the solute, such that the dimensional characteristics of each solute residue are uniformly related to the size of the original droplet, measuring the dimensions of the remaining solute residues and then calculating the size and size distribution of the original aerosol droplet.

The invention additionally envisages a method of providing a desired particle size distribution in an aerosol comprising initially measuring droplet size and size distribution in an aerosol and then adjusting the aerosol parameters to provide for a desired particle size range distribution.

The preferred method of solvent removal is by freeze drying so that crystallization of the solute occurs. Preferably, the freeze drying is rapid.

When crystallization does not occur the solute solids can still under suitable freeze drying techniques the shape of the droplet but there is a tendency for contraction. But I have found that the contraction over the whole droplet range in any one sample is proportional to the size of the original droplet.

In an aerosol which does not include a solute of suitable crystallisation characteristics it is envisaged within the invention that such will be added.

BRIEF DESCRIPTION OF THE DRAWINGS

The preferred embodiment will now be described by way of example and with reference to the accompanying drawings in which FIG. 1 is a diagram showing particle size distribution as a percentage of total volume for one nebuliser, and in which FIG. 2 shows the particle size distribution for a nebuliser used according to the teaching of U.S. co-pending application Ser. No. 602332.

FIG. 6 is a diagrammatic representation of a conventional gold depositer which may be used in the invention.

BRIEF DESCRIPTION OF THE PREFERRED EMBODIMENT

Figures 3A, 3B:
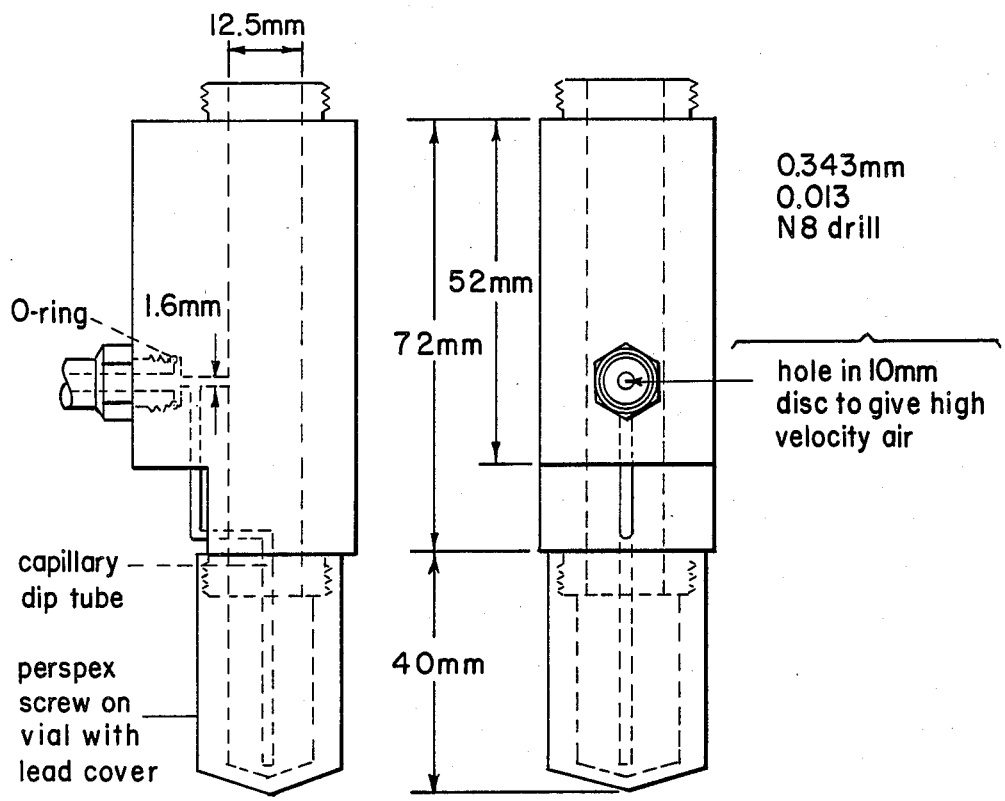
FIGS. 3($a$), 3($b$), and 3($c$) are diagrammatic representations of a conventional aerosol nebuliser dispenser which may be used for preparing aerosol droplets in accordance with the method of the invention.
Figure 3C:
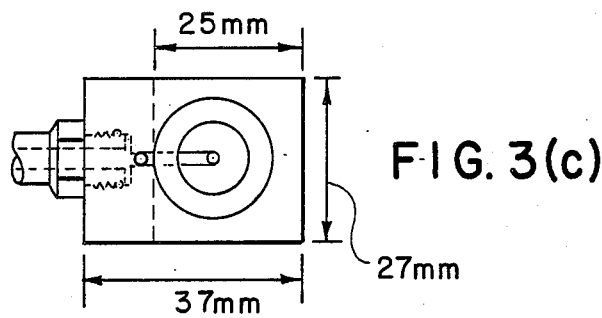
Figure 4:
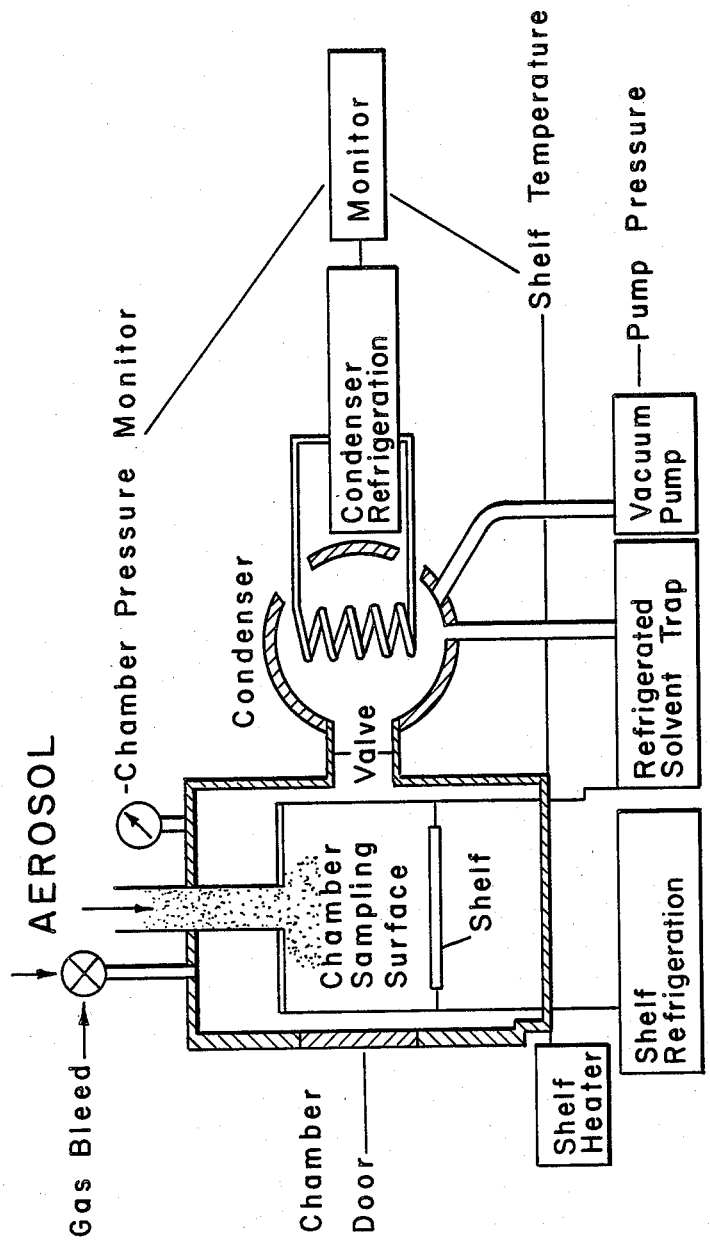
FIG. 4 is a diagrammatic representation of a conventional freeze drier that may be used in the invention.
Figure 5:
FIG. 5 shows droplet solute crystal residues formed by the method of the invention.
Figure 7:
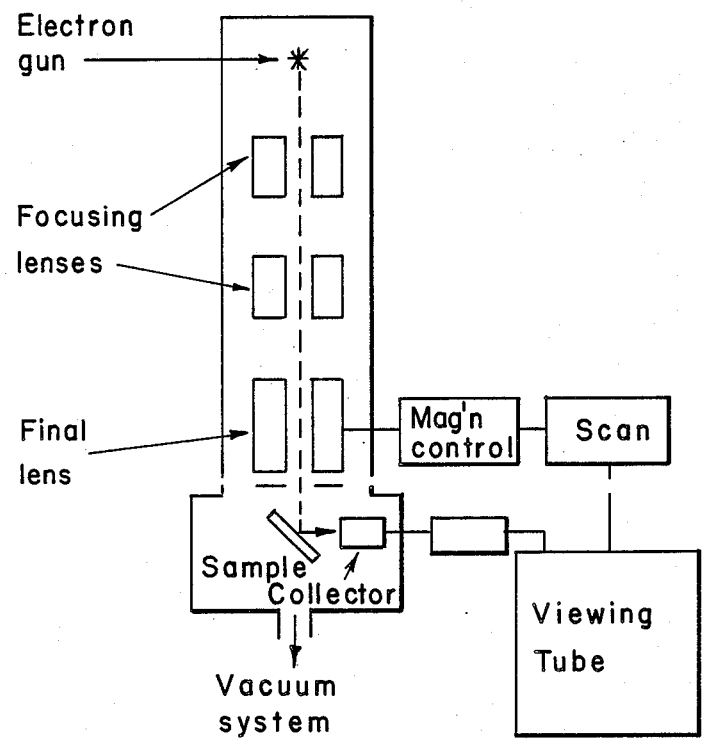
FIG. 7 is a block diagram of a conventional scanning electron microscope that may be used in the invention.

According to the preferred embodiment, aerosols are prepared for diagnosing lung tumors according to the method of co-pending U.S. co-pending application Ser. No. 602332, in which droplets of between 0.2 and 1.4 microns are preferred. The aerosol in a preferred embodiment contains, inter alia, approximately 10% lactose in water as solvent. The aerosol is formed by an aerosol dispenser as shown in FIGS. 3($a$)–3($c$) and is caused to be deposited on a plate, having a hydrophobic surface which causes the droplets to maintain surface tension, and reduces to a minimum the dimensional distortion of the droplets on contact with the plate. Prolongation of deposition time results in superpositioning of new droplets on deposited droplets with coalesence of the droplets, which is to be avoided. Coalesence of droplets, if permitted, gives a distorted view of original droplet size on analysis. The time is dependent upon such as the aerosol pressure and size of the plate. The time can be readily determined by trial and experiment. The plate bearing the droplets is then subjected to freeze drying by a freeze drier as shown, for example, in FIG. 4 until the water is substantially removed leaving inter alia lactose crystals as shown in FIG. 5. The plate is then prepared for scanning electron microscopy such as by gold deposition in a vacuum by using a gold depositer as shown in FIG. 6. Gold deposition in a vacuum on samples for scanning electron microscopy is well known to those skilled in the art. Direct current spattering or evaporation may be used; vacuum coating results in a deposition rate of the order of 0.1 nm$^{-1}$ (See Echlinp: "Use of the scanning electron microscope," Pergamon Press London 1922). The plate is then scanned by electron micrography by using a scanning electron microscope as shown in FIG. 7. The resultant micrographs are then examined and subjected to measurement and statistical analysis to thereby calculate the original droplet dimension characteristics of the aerosol.

It is to be appreciated that one of the measuring techniques is that of spread factor analysis, well known in the art from analysis of surface tension of droplets in detergent studies, and which provides an estimate of the original diameter of a droplet prior to deposition from measurements taken after deposition.

It is to be appreciated also that by the method of this invention measurements of size are made directly of the droplet residue, and not indirectly by means such as photometry.

The accuracy of this analysis is dependent on the degree of homogeneity of solute in the solvent of the aerosol. With a composition in which the solute is uniformly distributed, accuracy is greatly enhanced.

Preferably therefore this invention envisages the use of as uniform a solution as possible.

Modifications and developments are envisaged and can be incorporated without departing from the scope or spirit of the invention.

The basic principle of the invention is as set forth in the statement of invention and the manifestation of the invention as described is intended to be by way of example only.

I claim:

1. A method of calculating the dimensions of aerosol droplets of a solution, which comprises removing solvent from aerosol droplets while retaining substantially all the solute residue of said droplets such that the dimensional characteristics of said solute residue are uniformly related to the size of said droplets, measuring the dimensional characteristics of said solute residue, and calculating the size and size distribution of said droplets.

2. A method as claimed in claim 1, wherein the solvent is water.

3. A method as claimed in claim 2, wherein before the solvent from the aerosol droplets is removed, said droplets are deposited on a plate with a hydrophobic surface.

4. A method as claimed in claim 3, wherein the solvent is removed by rapid freeze drying.

5. A method as claimed in claim 1, wherein the solvent is removed by rapid freeze drying.

6. A method as claimed in claim 1, wherein the solute is lactose.

7. A method as claimed in claim 1, wherein after removing the solvent from the aerosol droplets said solute residue is subjected to gold deposition in a vacuum, and then subjected to electron micrography, and wherein the dimensions of said solute residue are calculated by measurement and statistical analysis.

8. A method as claimed in claim 7, wherein the dimensions of the solute residue are calculated by spread factor analysis.

9. A method as claimed in claim 1, wherein the diameter size of the aerosol droplets is from about 0.2 to 3.0 microns.

10. A method as claimed in claim 1, wherein the diameter size of the aerosol droplets is from about 0.2 to 1.4 microns.

11. A method as claimed in claim 1, wherein the diameter size of the aerosol droplets is from about 0.6 to 1.0 microns.

12. A method as claimed in claim 1, wherein the solute is uniformly distributed in the solvent.

13. A method of providing a desired particle size distribution in an aerosol comprising initially calculating the dimensions of aerosol droplets of a solution by removing solvent from aerosol droplets while retaining substantially all the solute residue of said droplets such that the dimensional characteristics of said solute residue are uniformly related to the size of said droplets, measuring the dimensional characteristics of said solute residue, calculating the size and size distribution of said droplets, and then adjusting the aerosol parameters to provide for a desired particle size range distribution.

14. An aerosol dispenser in which the particle size distribution in the aerosol has been adjusted by initially calculating the dimensions of aerosol droplets of a solution by removing solvent from aerosol droplets while retaining substantially all the solute residue of said droplets such that the dimensional characteristics of said solute residue are uniformly related to the size of said droplets, measuring the dimensional characteristics of said solute residue, calculating the size and size distribution of said droplets, and then adjusting the aerosol parameters to provide for a desired particle size range distribution.

* * * * *